United States Patent [19]

Goodman et al.

[11] Patent Number: 4,552,764
[45] Date of Patent: Nov. 12, 1985

[54] PEPTIDES FOR CONTROL OF INTESTINAL MOTILITY

[75] Inventors: Irving Goodman; Robert B. Hiatt, both of New York, N.Y.

[73] Assignee: Research Corporation, New York, N.Y.

[21] Appl. No.: 577,450

[22] Filed: Feb. 6, 1984

Related U.S. Application Data

[63] Continuation of Ser. No. 488,631, Apr. 26, 1983, abandoned, which is a continuation of Ser. No. 307,638, Oct. 1, 1981, abandoned, which is a continuation of Ser. No. 175,325, Aug. 4, 1981, abandoned, which is a continuation of Ser. No. 1,473, Jan. 8, 1979, abandoned, which is a continuation-in-part of Ser. No. 935,598, Aug. 31, 1979, abandoned, which is a continuation of Ser. No. 881,819, Feb. 27, 1978, abandoned, which is a continuation of Ser. No. 787,141, Apr. 13, 1977, abandoned, which is a continuation-in-part of Ser. No. 627,777, Oct. 3, 1975, abandoned, which is a continuation-in-part of Ser. No. 523,806, Nov. 14, 1974, abandoned.

[51] Int. Cl.$^4$ .................... C07G 7/00; C07C 103/52
[52] U.S. Cl. ................................. 514/2; 260/112 R; 424/108; 424/109
[58] Field of Search ................... 260/112 R; 424/177, 424/108, 109

[56] References Cited

PUBLICATIONS

Chem. Abstracts, vol. 73, 1970, 43577t, Hiatt et al.
Science, vol. 178, 1972, pp. 419-421, Goodman et al.
Chem. Abstracts, vol. 85, 1976—effective date May 20, 1976, 154437q, Goodman et al.

Primary Examiner—Howard E. Schain
Attorney, Agent, or Firm—Scully, Scott, Murphy & Presser

[57] ABSTRACT

Peptides isolated from the bovine posterior pituitary gland are useful for the control of intestinal motility.

3 Claims, No Drawings

PEPTIDES FOR CONTROL OF INTESTINAL MOTILITY

This is a continuation U.S. application Ser. No. 488,631 filed Apr. 26, 1983 which is a continuation of Ser. No. 307,638, filed Oct. 1, 1981; which is a continuation of Ser. No. 175,325, filed Aug. 4, 1981; which is a continuation of Ser. No. 001,473 filed Jan. 8, 1979; which is a continuation-in-part of Ser. No.935,598, filed Aug. 31, 1979; which is a continuation of Ser. No. 881,819; filed Feb. 27, 1978; which is a continuation of Ser. No. 787,141, filed Apr. 13, 1977; which is a continuation-in-part of Ser. No. 627,777, filed Nov. 3, 1975; which is a continuation-in-part of Ser. No. 523,806, filed Nov. 14, 1974; all now abandoned.

BACKGROUND OF THE INVENTION

Coherin is a polypeptide complex isolated from the bovine neurohypophysis which has been shown to have a unique regulatory action on the small intestine of dog and man. This physiologic function has two phases. Coherin, when injected intravenously, immediately activates the inhibitory mechanisms in the small intestine producing a complete cessation of intestinal motility for periods lasting up to 40 minutes without loss of tone. This effect is dose-related, and can be achieved at a dosage measured in nanograms per kilograms of body weight. This physiologic property of coherin is a convenient basis for bioassay. The second phase of coherin activity follows the inhibitory phase and consists of a coupling of the electromotor performance of adjacent short segments of intestine, resulting in coherent motor patterns capable of propagating intraluminal contents in a caudad direction. In dogs that have been fasted more than 18 hours, it has been shown that the electromotor performance of adjacent short segments of intestine (3 cm in the jejunum, 0.6 cm in the ileum) is characterized by a lack of coordination or coupling. When the basic electrical rhythm (BER) and the mechanical events occurring in a segment of intestine are recorded, either by means of monopolar electrodes or by intraluminal pressure transducers, coordinated propagative activity can be identified. This can be done by measuring the time differential between events with multiple, equally spaced electrodes or balloons. Any mechanical or electrical activity that is propagated through the entire segment in the caudad direction can be identified by a constant time differential (phase lag) between electrical or muscular activity.

In this connection, attention is directed to the following publications:

1. Hiatt, R. B., Goodman, I., Sandler, B., Cheskin, H.: The effect of coherin on the basic electrical rhythm of the dog ileum in vivo. Am. J. Dig. Dis. 22 (2): 108, 1977;
2. Mendel, C., Jaeck, D., Grenier, J. F., et al: Action of coherin on the basic electric rhythm and propagation in the isolated profused canine jejunum. J. Surg. Res. 19: 403, 1975;
3. Hiatt, R. B., Goodman, I.: Peptide treatment of postgastrectomy obstruction. Arch. Surg. 111: 997, 1976;
4. Hiatt, R. G., Goodman, I.: Long-term results in the treatment of regional ileitis with coherin. Am. J. Gastroenterol. 67: 274, 1977;
5. Dauchel, J., Schang, J. C., Kachelhoffer, J., Eloy, R., Grenier, J. F.: Effects of some drugs on electrical activity of the gut in the postoperative period. Eur. Surg. Res. 8: 26, 1976.

The isolation of this polypeptide complex has been described. See:

6. Goodman, I., Hiatt, R. B.: Coherin a new peptide of the bovine neurohypophysis with activity on gastrointestinal motility. Science 178: 419, 1972.

Because of the properties described above, the polypeptide coherin possesses useful activity on the smooth muscle of the gastrointestinal tract and other tissues. More particularly, it is useful in the treatment of ileitis, colitis, spastic constipation, spastic diarrhea, diverticulitis, peptic ulcer, post gastric surgery obstruction, and other conditions where irregularity of the smooth muscle function is involved.

THE INVENTION

This invention is concerned with certain low molecular weight peptide units or subfractions which can be isolated from the coherin complex, and with the pharmaceutically acceptable salts of such peptides. It is concerned also with therapeutically useful compositions containing at least one such compound as the principal active ingredient together with a pharmaceutically acceptable carrier. Methods for the treatment of ailments such as those mentioned above, and other conditions associated with arrythmia of the intestinal tract are also within the scope of the invention. One of the peptides of this invention, Coherin B, in addition to its utility for the control of intestinal motility, also manifests a high degree of vasoconstrictor activity. The product and its pharmaceutically acceptable salts, therefore, are useful in treatment of shock, and other conditions where it is necessary or desirable to effect contraction of the capillaries and arteries.

In describing this invention, reference will be made to the following entities:

Coherin, or the coherin complex which is the product isolated as described in Science, Infra.

Coherin A, B and C which are fractions which may be obtained, for example, from coherin by continuous electrophoresis.

Coherin $A_1$ and $A_2$ which are fractions which may be obtained, for example, by continuous electrophoresis of coherin A.

All fractions are enteroactive. Coherin B has a high order of vasoconstrictor activity, as stated above, in addition to its ability to control intestinal activity.

For convenience, the methods of isolating the coherin complex and the various subunits are summarized in Table I.

TABLE 1

| | ISOLATION OF COHERIN COMPLEX AND OF ITS PRODUCTS OF ELECTROPHORETIC DISSOCIATION | | | |
|---|---|---|---|---|
| Procedure | A | B | C | D |
| 1. Initial extraction of posterior pituitary powder | 0.2 M ammonium acetate; filtration and centrifugation | No change | No change | No change |
| 2. DEAE cellulose | Equilibration with | No change | No change | Elution with 0.05 M NH$_4$OAc |

TABLE 1-continued
ISOLATION OF COHERIN COMPLEX AND OF ITS PRODUCTS OF ELECTROPHORETIC DISSOCIATION

| Procedure | A | B | C | D |
|---|---|---|---|---|
| column | 0.2 M NH$_4$OAc; elution 0.05 M NH$_4$OAc, pH 5.6 | | | on H$_2$O washed column |
| 3. Sephadex G-50 column | Elution with 0.05 M NH$_4$OAc, pH 5.6 | No change | No change | No change |
| 4. Sephadex G-25 column | Elution with 0.05 M NH$_4$OAc, pH 5.6 | Lyophilization of eluate followed by isopropanol extrac. | Same as B | Isopropanol extraction used when necessary to convert syrup to powder |
| 5. Sephadex G-10 column | Elution with 0.05 M NH$_4$OAc, pH 5.6 | Elution with 0.1 M acetic acid | Same as B | Same as B |
| 6. Electrophoresis | Continuous on paper; pH 6; pH 3.5; pH 2.8 | Continuous on paper; pH 2.8; pH 3.5 | Continuous on paper; pH 2.0, 2.8, and 3.5 | Horizontal gel slab electrophoresis on Sephadex G-50; pH 2.8, 3.5, 6.0. |

Procedure A is the procedure of the Science article infra. A more detailed description of the procedure follows.

In step 1, acetone dried bovine posterior pituitary powder (50 g), is homogenized for 5 minutes in 2×125 ml of ammonium acetate (0.2 M, pH 5.6) in an ice bath. After centrifugation for 40 minutes at 18,000 g and 5° C. the supernatant solution is filtered through 3 g of diatomaceous filter aid (Celite, Johns Manville, Analytical), and transferred (step 2) to a column (50×610 mm) of diethylaminoethyl cellulose (DEAE) (Whatman, DE 23) that had been pre-equilibrated with the 0.2 M ammonium acetate. The DEAE column is eluted with 0.05 M ammonium acetate pH 5.6 and the eluate collected in fractions which are assayed for activity as measured by inhibition of intestinal contraction and by coherence of contraction in adjacent segments of intestine in the dog with Roux-en-Y fistula.

The main biological activity is eluted from DEAE cellulose in the fraction between 1825 and 3965 ml (total volume, 2140 ml; $\Sigma$A280/ml=4608).

The active fraction obtained from the DEAE cellulose column is lyophilized. Two grams of the solid are dissolved in 10 ml ammonium acetate (0.05 M, pH 5.6) and transferred to a column (50×610 mm) of cross-linked dextran gel (Pharmacia Corp., Sephadex G-50, Superfine).

In step 3, elution is achieved using 0.05 M ammonium acetate, pH 5.6 The active fraction is eluted between 1460 and 2580 ml (Ve/Vo=3.08).

The fraction eluted from Sephadex G-50 is lyophilized and the product (2.1 g) dissolved in 0.05 M ammonium acetate (5 ml); the solution is applied as above to (step 4) a column (50×1090 mm) of cross-linked dextran gel (Pharmacia, Sephadex G-25 Superfine) and eluted as above. The active component is located in the fractions between 1460 and 2580 ml (Ve/Vo=2.33).

In an analogous manner, the active fraction obtained from Sephadex G-25 is lyophilized, dissolved in 4 ml of acetic acid, 0.1 M, and transferred (step 5) to a column (10×1050 mm) of highly crossed-linked dextran gel (Sephadex G-10) which is pre-equilibrated with the same solvent.

Coherin isolated in step 5 appears to exist as a complex bound either by electrostatic or Van der Waals forces. It is obtained upon elution, as above, of the product of step 4 from Sephadex G-10 at a rate of 0.5 ml per minute in fractions between 248 ml and 363 ml (Ve-Vo×1.47). Purification of bound coherin is achieved by dissolving 78 mg of the product of step 5 in 19 ml acetic acid, 0.2 M. This solution is extracted (3×10 ml) with butanol-acetic acid-water (4:1:5), upper (non-aqueous) phase. The non-aqueous extracts are combined and concentrated in vacuo to a white solid. The solid is dissolved in 10 ml ethanol, 95% and upon standing at 5° for 48 hours formed fine white crystals.

Coherin complex remains bound after repeated recycling on Sephadex G-10 in acetic acid, 0.1 M.

The complex acts as a substantially homogeneous entity when subjected to paper electrophoresis at pH 6. It acts in the same manner at pH 3.5 and 2.8.

The coherin complex isolated in step 5 undergoes dissociation to yield coherin A, B and C when subjected to repeated cycles, for example 4 to 10 cycles, of continuous flow electrophoresis on paper at pH 2.8 and 3.5 as described below. This modification of Procedure A is not shown in Table 1.

Using the Beckman-Spinco Continuous Flow Electrophoresis apparatus, Model CP, coherin complex (step 5) ($\Sigma$A280×175) is dissolved in acetic acid, 0.2 M, pH 2.75 to give a concentration such that A280×4.0; this solution is applied at a point +75 mm (anodal) from vertical midline at the rate of 0.42 ml per hour (18 V/cm; 0.83 mA/cm). The electrolyte is 0.2 M acetic acid and elution rate was 1.2 ml per tube per hour.

Coherin A is located in fractions 13 to 19 which correspond to drip tips 95 mm cathodal to the point of application. The solid obtained after pooling and lyophilization of these tubes is extracted with isopropanol (3×3 ml) and collected by centrifugation.

Under these conditions (pH 2.8) Coherin B is isolated in fractions 5 to 9, 150 mm cathodal to the point of application and Coherin C is eluted in fractions 17 to 19, (60 mm cathodal to the point of application).

Tubes from several runs which contain coherin A, B and C respectively, all obtained as described above, are pooled, lyophilized and individually recycled four times to electrophoretic homogeneity on the continuous flow electrophoresis apparatus at pH 2.8 and 3.5. The electrolyte for pH 3.5 was ammonium acetate, 0.02 M in acetic acid, 0.2 M. Upon recycling at pH 3.5 coherin A is located in fractions 19–21, B in fractions 15 to 19 and C in 23 to 25. Since the fraction numbers on the Beckman-spinco Model CP remain stationary, they indicate the position relative to the anode and cathode. The numbers are from 1 to 32 from cathode to anode.

Coherin A, B and C are isolated in substantially pure form after repeated recycling (e.g. 8 to 12 recyclings) on continuous flow electrophoresis at pH 2.8 and 3.5 followed by ethanolic extraction to remove traces of other peptides and free amino acids.

Coherin A, B and C can also be isolated by Procedure B of Table 1.

In this procedure, the eluate from step 3 is first lyophilized and then extracted with isopropanol. The residue is taken up in acetic acid, and passed over a Sephadex G-10 column equilibrated with the same acid. It is eluted with 0.1 M acetic acid. The eluate is then subjected to continuous flow electrophoresis for 8 to 12 passes at pH 2.8 and 3.5 to isolate the desired subunits.

Procedure B is repeated in Procedure C up to the electrophoresis step. The eluates from step 5 containing coherin A, B and C are then pooled, lyophilized and individually recycled on continuous flow electrophoresis. Each pool is sufficiently large to permit recycling 8 to 12 times at each of pH 2.0, 2.8 and 3.5. Under these conditions, coherin B and C retain their homogeneity, but A dissociates to yield two fractions, $A_1$ and $A_2$.

Procedure D outlines another method, the gel slab electrophoresis method, for obtaining coherin $A_1$, $A_2$, B and C. The minor differences in steps 1 through 5 are shown in the table. The principal difference is in step 6.

In a typical example, 100 g Sephadex G-50 superfine is allowed to swell in water and washed with 5 liters 0.2 M atetic acid in a column (6×100 cm). 230 ml of the washed gel is transferred to a polyacrylic tray (19×20.2×2.4 cm) to form a dense layer, 6 mm in depth. Using the Research Specialties Co. electrophoresis apparatus, the tray is placed in position on the water-cooled platform and a wick of Whatman 3 MM filter paper (18.5×27 cm) inserted into the gel at each end. The free ends of the wicks are inserted into the anode and cathode vessels respectively. The sample (ΣA280×21) in 1.0 ml 0.1 M acetic acid is applied in 50 μl aliquots along the midline of the gel by micropipette. 10 μl of bromophenol blue ($10^{-4}$ M in 0.1 M HAc) is applied at the midline for reference. To retard evaporation, the tray is covered with a glass plate (20×20 cm). Electrophoresis is continued for 6 hours at 12°, 30 v/cm, 0.56 mA/cm. To locate peptide components, test strips of Whatman 3 MM filter paper (1×20 cm) are inserted into the gel parallel to the direction of current flow, quickly removed, dried and treated with fluorescamine. Five bands cut from the gel slab, transferred to glass chromatograph columns (2×30 cm) and eluted with 0.1 M acetic acid (150 ml per fraction). Eluates are lyophilized. The fractions are identified by assay for biological activity. They may be examined for homogeneity by paper electrophoresis and by chromatography on thin layers of Sephadex G-50 and of silica gel using the procedures described above. The procedure may be repeated at a different pH, for example 3.5, to improve the homogeneity of the fractions.

The salient properties of the coherin subunits are summarized in Table 2. Their amino acid substituents are set forth in Table 3.

The subunits described are all highly soluble in water and aqueous buffer solutions. They are slightly soluble in absolute ethanol and insoluble in acetone or ether. They are also remarkably thermostabile. For example, they may be heated at about 100° C., and still remain highly active. They are stable in the presence of mercaptoethanol.

TABLE 2

| AMINO ACID COMPOSITION OF COHERIN PEPTIDES* | | | | |
|---|---|---|---|---|
| Amino Acid | $A_1$ | $A_2$ | B | C |
| Asp | 1 | | 1 | 3 |
| Thr | | | | 2 |
| Ser | 1 | 1 | 1 | 2 |
| Glu | 1 | | 1 | 4 |
| Pro | 1 | | 1 | 2 |
| Gly | 1 | 1 | 1 | 3 |
| Ala | 1 | | 1 | 3 |
| Val | | | | 2 |
| Ile | | | | 1 |
| Leu | 1 | | 1 | 3 |
| Nle | | | | |
| Tyr | | 1 | | 1 |
| Phe | | | 1 | 1 |
| His | | | | 1 |
| Lys | | | 1 | 3 |
| Trp | | | | |
| Arg | | | 1 | 1 |

*Molar ratios to nearest whole number.

TABLE 3

| PROPERTIES OF COHERIN PEPTIDES | | | | | |
|---|---|---|---|---|---|
| | A | $A_1^{(a)}$ | $A_2^{(a)}$ | B | C |
| λ max (nm) pH 3.5 | | 270 | 273 | 276 | 277 |
| λ min (nm) pH 3.5 | | 258 | 247 | 249 | 253 |
| λ max (nm) pH 1 | 274 | | | 276 | |
| λ max (nm) pH 11 | 240,290 | | | 239,290 | |
| λ min (nm) pH 1 | 248 | | | 253 | |
| λ min (nm) pH 11 | 233,272 | | | 236,276 | |
| $A_{280}^{1\%}$ pH 1 | 12.1 | | | 18.5 | |
| $A_{280}^{1\%}$ pH 3.5 | | 6.7 | 13.5 | 3.2 | 5.3 |
| Electrophoresis $r^{(b)}$ | | | | | |
| pH 2.0 | −2.22 | −2.93 | −2.47 | −3.27 | −2.07 |
| pH 3.5 | −1.83 | −1.71 | −1.60 | −2.49 | −1.02 |
| pH 8.5 | +0.39 | | | −1.16 | |
| pH 11.0 | | +0.85 | +1.02 | +0.52 | +0.62 |
| Isoelectric point$^{(c)}$ | 6.0 | 6.0 | 6.5 | 8.5 | 6.0 |
| $R_f^{(d)}$ | | | | | |
| (1) | .70 | .15 | .61 | .29 | .15 |
| (2) | .33 | .16 | .47 | .03 | 0 |
| $R_{Bac}^{(e)}$ | | 81 | 77 | 93 | 121 |
| Mol. Wt.$^{(f)}$ | 300–600 | 600–1000 | 300–600 | 1000–1500 | 2900–3500 |
| Dose for 5 min. inhibition (μg/kg)$^{(g)}$ | 0.5 | 0.05 | 10 | 0.05 | 10 |

NOTES FOR TABLE 3 a. Isolation from human as well as bovine pituitary glands.

b. Electrophoresis is on Research Specialties Co. apparatus using Whatman 3 MM paper and electrolyte buffers as follows:

pH 2 Formic, acetic acid (14.2 V/cm 0.85 mA/cm)

pH 3.5 Pyridine, Acetic acid (14.5 V/cm 0.85 mA/cm), or ammonium acetate, 0.05 molar, or triethyl ammonium acetate, 0.05 molar pH 8.5 Barbital buffer 0.05M (8.13 V/cm, 1.25 mA/cm), or diethylamino ethanol, 0.05 molar pH 11.0 Na$_2$CO$_3$, 0.05 M (8.13 V/cm, 1.25 mA/cm)

$$r = \frac{\Delta M_s}{M_{BPB}}$$

where $\Delta M_s$ is the difference (in mm) in migration between bromphenol blue and the sample, and $M_{BPB}$ is migration of bromphenol blue.

c. Isoelectric point is taken as the pH at which migration from the origin is zero using the electrophoresis apparatus described in (b).

d. Chromatography is on thin layers of silica gel (Merck, Silica gel G) on glass and on Eastman chromagram sheets. Solvents (1) n-Butanol-pyridine - acetic acid - H$_2$O (60:40:12:48). (2) n-Butanol-acetic acid-water (4:1:1).

e. R$_{Bac}$ × Migration distance of sample (nm × 100) ÷ migration distance of bacitracin A.

f. Molecular weights are estimated on the basis of migration ratios on thin layers of dextran gels (Sephadex G-50) together with amino acid analyses.

g. Bioassays are run routinely on major fractions isolated in all steps described above. Dogs were surgically prepared with Roux-en-Y fistulae allowing intestinal contractions to be monitored by pressure transducers in the lumen of a segment of ileum. Coherin activity was determined by mechanical as well as electrical means. Activity of fractions was indicated by marked inhibition of intestinal contraction within 30 seconds after intravenous injections of coherin. Fractions for assay were routinely dissolved in normal saline solution.

Since the compounds of this invention are amphoteric, both pharmaceutically acceptable metallic salts and acid addition salts can be prepared and are useful. Typically useful salts include the salts of alkali and alkaline earth metals, particularly calcium, sodium and potassium, ammonium and amine salts such as cyclohexylamine and piperidine salts, and organic and inorganic acids such as hydrochloric sulfuric phosphoric acetic, lactic, citric, tartaric, oxalic, succinic, maleic, gluconic, and the like. The compounds may be prepared by conventional procedures normally utilized for the preparation of such salts, for example by titration of aqueous solutions with an acid or base and removing the water by freeze drying. Alternatively, they can be taken up in water, the appropriate acid or base added, and the salt precipitated by the addition of a water miscible non-solvent such as acetone.

It is recognized, of course, that a number of simple derivatives can be prepared by acylation of free hydroxyl groups or amino groups, or by esterification of free carboxyl groups on the basic peptides of this invention. These compounds are within the scope of the invention. They are readily prepared by procedures well known to those skilled in the art.

The products of this invention may be administered alone, but will generally be administered with pharmaceutically acceptable, non-toxic carriers, the proportions of which are determined by the suitability and chemical nature of the particular carrier, the chosen route of administration, and standard pharmaceutical practice. For example, they may be administered orally in the form of tablets or capsules containing such excipients as starch, milk sugar, certain types of clay, etc. They will normally be enteric coated so as to be more resistant to the acid and digestive enzymes of the stomach. They are, in fact, resistant to gastrointestinal enzymes, such as pepsin and chymotrypsin and partially resistant to trypsin. However, since they are of relatively low molecular weight, they may be absorbed before they are hydrolyzed by the proteolytic enzymes of the stomach. For intravenous, intramuscular, or subcutaneous administration, they may be used in the form of sterile solutions containing other solutes, for example, enough saline or glucose to make the solution isotonic. A wide variety of dosage unit forms are possible.

The physician or veterinarian in attendance will determine the dosage regimen which will be effective. This will depend upon such factors as the age and weight of the patient, the condition being treated, and the dosage unit form selected. Dosages as low as 0.1 to 10 μg/kg of body weight are satisfactory.

What is claimed is:

1. Coherin A$_1$ which is a thermally stable peptide characterized as containing aspartic acid, serine, glutamic acid, proline, glycine, alanine, and leucine, in a mole ratio of 1:1, soluble in water, slightly soluble in absolute ethanol and insoluble in acetone, having a molecular weight of from 600 to 1000, having a λ maximum of 270 nm of pH 3.5 with a corresponding minimum at 258 nm in the ultraviolet region of the spectrum, having the ability to control intestinal motility and the pharmaceutically acceptable salts thereof.

2. A therapeutic composition containing a compound of claim 1, together with a pharmaceutically acceptable carrier.

3. A method of controlling intestinal motility which comprises administering an effective amount of a compound of claim 1 to a host in need of such control.

* * * * *